(12) United States Patent
Dekker et al.

(10) Patent No.: US 6,569,900 B1
(45) Date of Patent: May 27, 2003

(54) FULVIC ACID AND ITS USE IN THE TREATMENT OF VARIOUS CONDITIONS

(75) Inventors: Johannes Dekker, Faerie Glen (ZA); Constance Elizabeth Medlen, Rietondale (ZA)

(73) Assignee: Enerkom (Proprietary) Limited, Pretoria (ZA)

( * ) Notice: Subject to any disclaimer, the term of this patent is extended or adjusted under 35 U.S.C. 154(b) by 0 days.

(21) Appl. No.: 09/807,004

(22) PCT Filed: Oct. 8, 1999

(86) PCT No.: PCT/IB99/01649

§ 371 (c)(1),
(2), (4) Date: Jul. 9, 2001

(87) PCT Pub. No.: WO00/19999

PCT Pub. Date: Apr. 13, 2000

(30) Foreign Application Priority Data

Oct. 8, 1998 (ZA) .............................................. 98/9190
Apr. 21, 1999 (ZA) .............................................. 99/2848

(51) Int. Cl.$^7$ ................................................ A01N 37/08
(52) U.S. Cl. ........................ 514/530; 514/570; 514/573
(58) Field of Search ................................ 514/530, 570, 514/573

(56) References Cited

FOREIGN PATENT DOCUMENTS

| | | |
|---|---|---|
| CN | A1097990 | 2/1995 |
| CN | A1213665 | 4/1999 |
| DE | A1-2850685 | 6/1980 |
| GB | A2244215 | 11/1991 |
| JP | A6087752 | 3/1994 |
| JP | A11009674 | 1/1999 |
| WO | A1-9749288 | 12/1997 |

*Primary Examiner*—Paul J. Killos
(74) *Attorney, Agent, or Firm*—Birch Stewart Kolasch & Birch LLP (57) ABSTRACT

Fulvic acid salts, esters or derivatives thereof in pharmaceutical preparations are effective for treating inflammation, acne, exzema or bacterial or fungal or viral infections. These pharmaceutical preparations may be given either orally or topically in the form of a solution, paste, ointment, powder to humans or animals.

8 Claims, 4 Drawing Sheets

Case 4 – Before treatment

FIG. 5B

Case 4 – Seventh day after treatment

FULVIC ACID AND ITS USE IN THE TREATMENT OF VARIOUS CONDITIONS

This application is the national phase under 35 U.S.C. §371 of PCT International Application No. PCT/IB99/01649 which has an International filing date of Oct. 8, 1999, which designated the United States of America.

FIELD OF THE INVENTION

This invention relates to fulvic acid and its use in the treatment of various conditions.

Humic substances are ubiquitous in nature and arise from the decay of plant and animal residues in the environment (MacCarthe et al. 1990). These substances can be divided into humic acid, fulvic acid and human on the basis of the solubility in water as a function of pH. Fulvic acid is the fraction that is soluble in water under all pH conditions and is in general lower in molecular size and weight and lower in colour intensity than humic acids.

Humic substances commonly account for 50% of the dissolved organic carbon concentrations in stream water, of which 90 to 95% are fulvic acids. Humic acids are 3 to 5 times more abundant in soils than fulvic acids (Stevenson, 1982), whereas fulvic acids are 9 to 10 times more abundant in water than humic acids (Malcolm, 1985).

Humic acids have been successfully used in the treatment of:

(i) hyperacidity and other gastric disturbances in humans (Reichert, 1966, Gramsch, 1961)

(ii) inflammation (Salz 1974, Motohisa et al., 1974)

(iii) anemia and hypercholesterolemia (Soloveyva and Lotosh 1984)

(iv) Von Willebrand disease (Lopez-Fernandez et al., 1992)

The possible application of fulvic acid in the treatment of human and animal diseases has, up to now, not been investigated.

Wang et al (1996) studied the interaction between fulvic acids and active oxygen free radical and found fulvic acids from peat were able to scavenge both superoxide and hydroxyl radical. It has also been shown that fulvic acids prevent the absorption of mutagens through the rat small intestine using a highly mutagenic furanone found in chlorinated water and an in vitro everted rat gut sac system (Clark and Chipman, 1995).

Although the presence of fulvic acids in the drinking water of certain parts of China has been coupled to the incidence of Kashin-Beck disease, this only occurred in conjunction with a selenium deficient diet (Peng and Xu, 1987).

U.S. Pat. Nos. 4,999,202 and 5,204,368 disclose compositions having bacterial and bacteriostatic properties containing a fulvic acid, salt or derivative thereof as the active ingredient. These compositions are described as being useful as disinfectants.

SUMMARY OF THE INVENTION

According to one aspect of the invention, there is provided a pharmaceutical composition comprising a fulvic acid, salt, ester or derivative thereof as the active ingredient.

The pharmaceutical composition may be provided for oral or topical administration to a subject.

In the case of topical administration, the composition may be provided in the form of a solution, paste, ointment, powder or any other form suitable for topical administration.

The subject may be a human or an animal.

Further according to the invention, there is provided the use of a fulvic acid, salt, ester or derivative thereof, in the treatment of a condition of a subject. The condition may, for example, be inflammation, acne, eczema or bacterial or fungal or viral infections.

The treatment of the condition may be by oral or topical administration.

The subject is typically a human or an animal.

The fulvic acid is preferably a fulvic acid derived from a wet coal oxidation process of the type described in U.S. Pat. No. 4,912,256. Such a fulvic acid is hereinafter referred to as "oxifulvic acid or OFA".

Bergh et al. (1997) identified almost 50 different compounds, most of which were carboxylic acids, in oxifulvic acid. The compounds were mostly ordinary physiological metabolites with no evidence of any toxic compound in the product mixture.

A typical functional group analysis of oxifulvic acid is given below:

Total acid groups: 11.5–15.5 meq/g

Carboxylic groups: 8.5–12.5 meq/g

Phenolic groups: 2.3–3.7 meq/g

In an example of the invention, a composition for topical application to a human or animal Comprises 4.5 percent, or 9.0 percent, by mass of oxifulvic acid in an aqueous cream.

DESCRIPTION OF EMBODIMENTS

The active ingredient in the practice of the invention is a fulvic acid, salt, ester or derivative thereof. Oxifulvic acid, having the preferred functional group analysis mentioned above, has been subjected to a number of in vitro and in vivo studies and these are described hereinafter.

The Effects of Oxifulvic Acid on Immune Functions In Vitro

The Effects of Oxifulvic Acid on the Production of Oxidants by Human Neutrophils.

Human neutrophils (separated on Ficoll) were treated with oxifulvic acid (at 12.5 and 25 ug/ml) for 15 min at 37° C. The cells were stimulated with PMA (phorbol myristate acetate) (20 ng/ml) and superoxide production determined by measuring the superoxide-inhibitable reduction of ferricytochrome C (1 mM). A significant inhibition of superoxide production was observed at both concentrations tested (Table 1).

TABLE 1

The effects of oxifulvic acid on PMA-activated neutrophil superoxide production

| Treatment | nmoles superoxide/ $10^6$ neutrophils/10 min* |
|---|---|
| Resting | |
| Control | 0.072 |

TABLE 1-continued

The effects of oxifulvic acid on
PMA-activated neutrophil superoxide production

| Treatment | nmoles superoxide/ $10^6$ neutrophils/10 min* |
|---|---|
| Stimulated (+PMA) | |
| Control | 67.2 |
| + oxifulvic acid (12.5 ug/ml) | 59 |
| (25 ug/ml) | 43 |

*average data of two experiments

The superoxide scavenging activities of oxifulvic acid (at 25 ug/ml) were determined using the hypoxanthine (1 mM)/xanthine-oxidase (100 mU/ml) enzymatic system to generate superoxide. Oxifulvic acid exhibited superoxide-scavenging activity (Table 2).

TABLE 2

Superoxide scavenging activities of oxifulvic acid at 25 ug/ml.

| Treatment | nmoles superoxide* |
|---|---|
| Control | 55.95 |
| Oxifulvic acid | 41.25 |

*average data of two experiments

Figure 1:
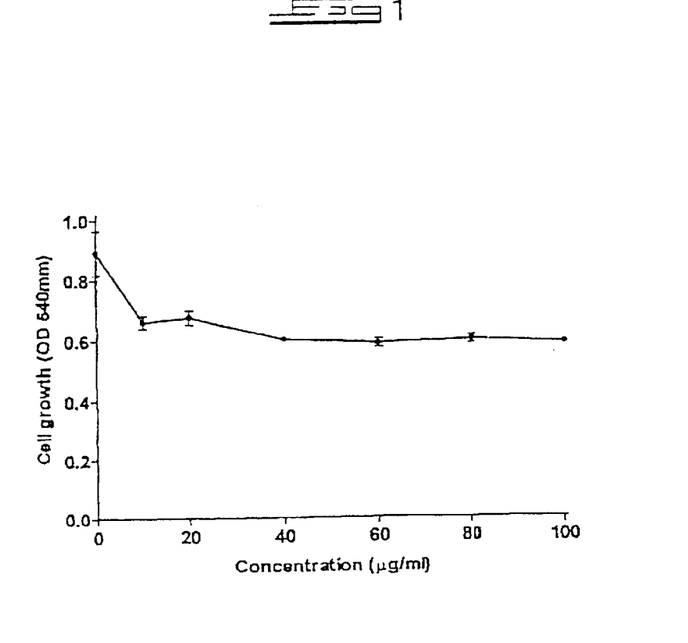
FIGS. 1 to 4 illustrate graphically the results of certain tests carried out on oxifulvic acid.

The Effects of Oxifulvic Acid on the Proliferative Response of a Mixed Lymphocyte Culture These experiments were performed by co-culturing the lymphocytes of two different donors in both the presence and absence of serial dilutions of the experimental agent for 7 days. Oxifulvic acid caused a dose-related inhibition of cell growth (FIG. 1).

The Effects of Oxifulvic Acid on Interleukin 2 (IL-2) Production by Human Lymphocytes Phytohemaglutinin (PHA)-stimulated human lymphocyte cultures were treated with oxifulvic acid at 60, 80 and 100 µg/ml for 2 days, whereafter the cells were centrifuged and the supernatant assayed for IL-2 levels, using a Biotrak TM human interleukin 2 ELISA system from Amersham TM (Amersham International Plc, Buckinghamshire, England).

Figure 2:
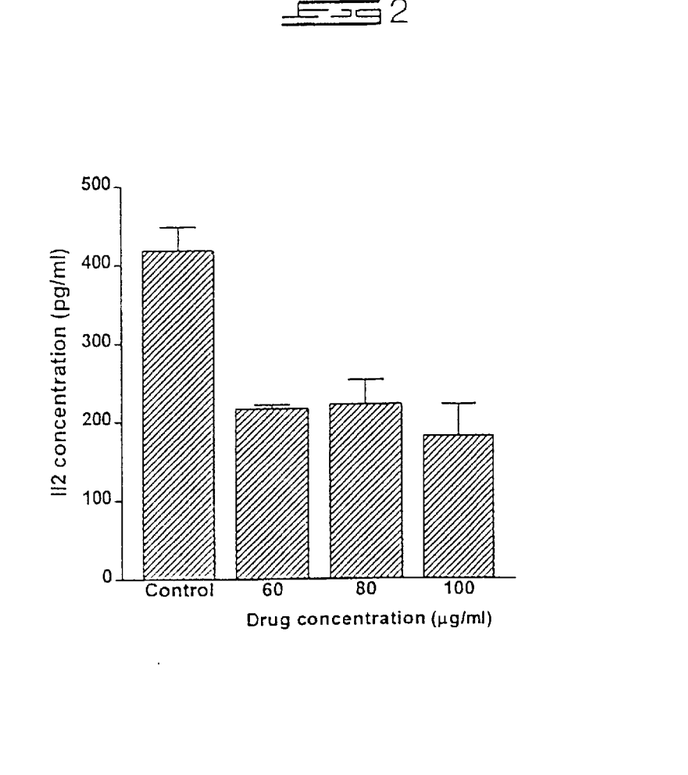

Oxifulvic acid caused a statistically significant decrease in IL-2 production by stimulated lymphocytes at all three concentrations tested (FIG. 2).

Evaluation of Oxifulvic Acid as an Anti-Inflammatory Compound In Vivo

1. Evaluation in Dinitrofluorobenzene Sensitized Mice

The effects of oxifulvic acid (4.5 and 9% cream applied topically) in 2,4-dinitro-1-fluorobenzene (DNFB) sensitized mice were evaluated using 50 BALB C female mice (6–7 weeks old) according to the method described by Rheins et al (1987). The mice were sensitized by application of DNFB to the shaved abdomen, divided into 5 groups and challenged on the right ear 6 days later. The inflamed ears of the mice in each group were treated topically for two days with one of the following creams i.e. control cream, oxifulvic acid 4.5%, oxifulvic acid 9%, dichlophenac sodium 1% (Voltaren Emulgel®) and betamethasone 0.1% (Betnovate®). The thickness of the ear was measured with a clock gauge before the challenge and 24 and 48 h later.

Figure 3:
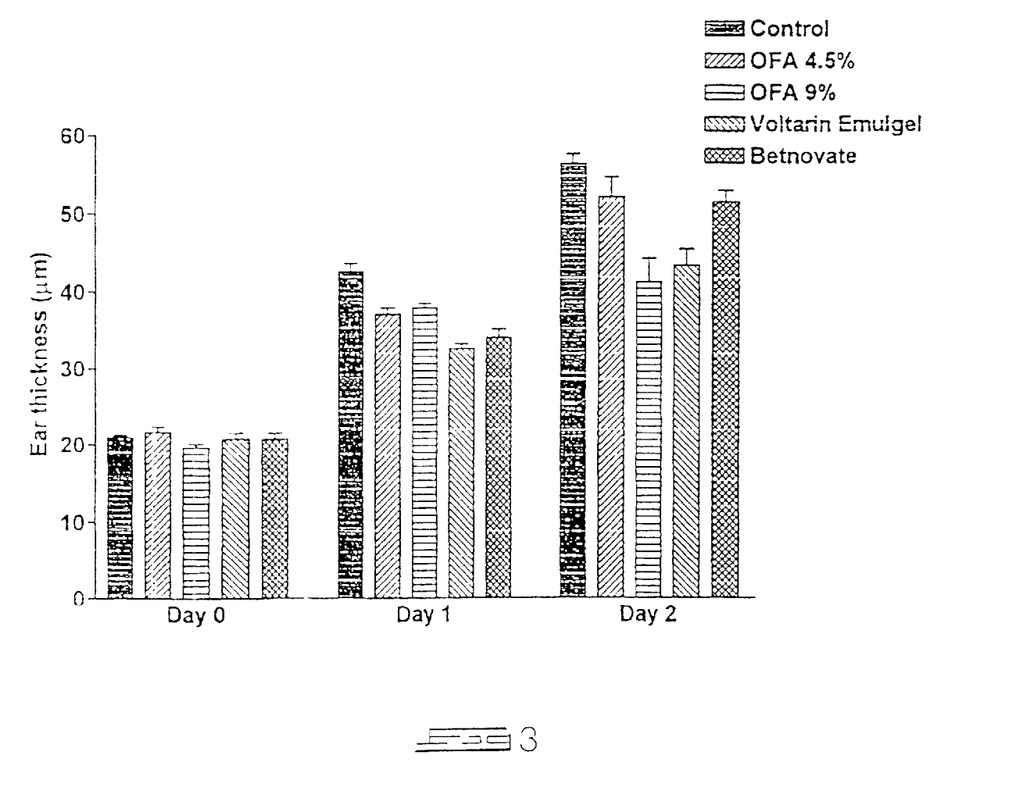

All four treatments caused a significant decrease in inflammation on both days (FIG. 3). These results were confirmed microscopically after termination of the mice and embedding the affected ears in paraffin wax.

No signs of toxicity was observed during the two days of treatment with the two oxifulvic acid creams.

Figure 4:
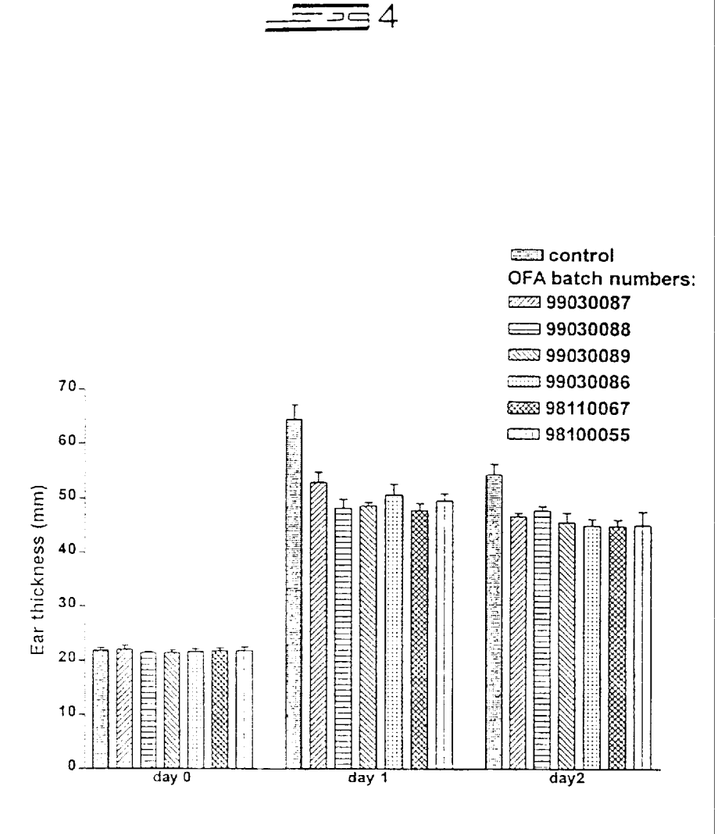

An experiment was also carried out to study the possible variation between creams derived from oxifulvic acid batches sampled from different runs (98100055 and 98110067) as well as from different batches (99030086 to 99030089) sampled on consecutive days from the same continuous run. In this study 7 groups of 5 mice per group were used. The first group was treated with control cream whereas the other 6 groups were treated with the above-described 6 different 9% oxifulvic acid creams. The results of this experiment are reflected in FIG. 4.

Again no sign of toxicity was observed during the two days of treatment with the six oxifulvic acid creams.

Similar results were obtained as in the previous experiment. Oxifulvic acid, once again, caused a statistically significant inhibition of inflammation in this model. An analysis of variance (two-way ANOVA) was performed on the results obtained with the different oxifulvic acid creams. For day one the P value is 0.131 and day two 0.761. There was, therefore, no significant difference between the various samples tested.

2(a) Evaluation in Pyotraumatic Dermatitis in Cats and Dogs

This trial was done by Dr O J Botha, Hatfield Bird and Animal Hospital, Pretoria. Ten clinical cases were entered in the trial. To qualify for this trial the following entities had to be present on the skin of the animals: wheal, erythema, pruritis and pyogenesis. Lesions were classified as slight, mild or severe before treatment. No other treatment was allowed during the trial. Owners were supplied with the 9% oxifulvic acid cream and instructed to apply the cream twice a day to the affected areas. This treatment had to continue for seven days. The owners were asked to return exactly seven days after the treatment commenced and the cases were reevaluated clinically, biopsied and photographed.

Figure 5A:
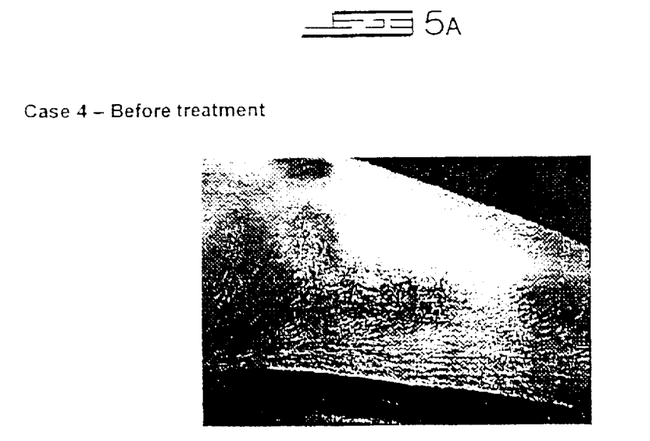
FIGS. 5A and 5B illustrate photographically the results of treating pyotraumatic dermatitis using an oxifulvic acid cream of the invention.
Figure 5B:
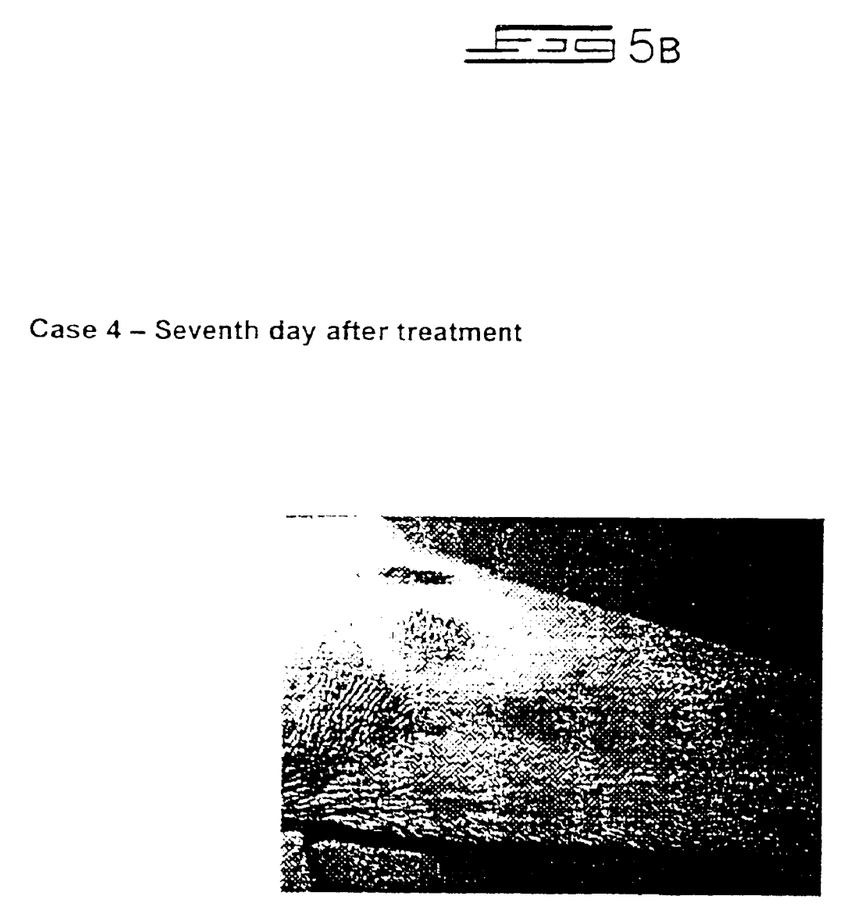

Decreased inflammation was observed clinically as well as pathologically in all 10 cases studied as can be seen from the histopathological investigation described hereinafter. No side effects were noted in any of the cases. In most cases it was noted that resolutions of the lesions were complete and did not recur. Only in one of the cases, described as a chronic and longstanding case, did the owner return after 3 days because the dog was still scratching extensively. A short-acting cortisone was then administered and the dog responded favourably. A typical example of the results obtained during this trial can be seen in FIG. 5. These photographs were taken before and after the treatment of a dalmation dog with lesions on the left medial humerus. Before treatment (FIG. 5A) severe wheal, erythema and pyogenesis were noted while after treatment (FIG. 5B) an absence of erythema and pyogenesis and only very slight remaining wheal were noted. In addition, the biopsy lesions of the first biopsy were completely healed.

2(b) Histopathological Investigation: Skin Biopsies: Clinical Study: Topical Ointment—9% Fulvic Acid Cream Method Clinical cases having lesions of allergic dermatitis and wet eczema were identified in different species of animal as shown in Table 3.

TABLE 3

Information on clinical cases

| Lab no | Treatment group | Species |
|---|---|---|
| 3973 A1 | Control | Cat (house cat) |
| 3973 A2 | Treatment | Cat (house cat) |
| 3973 B1 | Control | Dog (Bull Mastiff) |
| 3973 B2 | Treatment | Dog (Bull Mastiff) |

TABLE 3-continued

Information on clinical cases

| Lab no | Treatment group | Species |
|---|---|---|
| 3973 C1 | Control | Dog (Bull dog) |
| 3973 C2 | Treatment | Dog (Bull dog) |
| 4991 A1 | Control | Dog (Dalmation) |
| 4991 A2 | Treatment | Dog (Dalmation) |
| 4991 B1 | Control | Dog (Maltese) |
| 4991 B2 | Treatment | Dog (Maltese) |
| 4991 C1 | Control | Dog (St. Bernard) |
| 4991 C2 | Treatment | Dog (St. Bernard) |
| 4991 D1 | Control | Dog (Maltese) |
| 4991 D2 | Treatment | Dog (Maltese) |

Biopsies of control lesions (prior to treatment) of approximately 3 mm were collected, fixed in formalin and followed up with biopsies as close as possible to the site of the previous biopsy following treatment.

The formalin-fixed skin-biopsies were processed according to standard routine methods used for histological studies, embedded in paraffin-wax and slices of 6 $\mu$m each were prepared. All slices were coloured using the Haemotoxillin and Eosine staining method.

Histopathological Findings

The histopathological findings are shown in Table 4. The control samples were initially investigated for specific morphological lesions which were graded as indicated in Table 4. The biopsies of the treated lesions were evaluated similarly.

It must be kept in mind that in each case each lesion could only be compared to its original control lesion, due to the fact that the specific ethiology and morphological changes differed in each of the cases.

TABLE 4

Histopathological findings: Clinical trials: Enerkom

| | |
|---|---|
| Case 3973 A1: Control lesion | Surface exudative dermatitis (3+) |
| | Ulceration (3+) |
| | Dermal inflammation (2+) |
| Case 3973 A2: Treated lesion | Surface exudative dermatitis (−) |
| | Ulceration (−) |
| | Dermal inflammation (1+) |
| Case 3973 B1: Control lesion | Hyperplastic epithelia (3+) |
| | Hyperpigmentation (2+) |
| | Dermal inflammation (3+) |
| Case 3973 B2: Treated lesion | Hyperplastic epithelia (−) |
| | Hyperpigmentation (1+) |
| | Dermal inflammation (1+) |
| Case 3973 C1: Control lesion | Surface exudation (3+) |
| | Hyperplastic epidermis (3+) |
| | Dermal inflammation (3+) |
| Case 3973 C2: Treated lesion | Surface exudation (−) |
| | Hyperplastic epidermis (3+) |
| | Dermal inflammation (1+) |
| Case 4991 A1: Control lesion | Ulceration and exudation (2+) |
| | Hyperplastic epidermis (2+) |
| | Dermal inflammation (2+) |
| Case 4991 A2: Treated lesion | Ulceration and exudation (−) |
| | Hyperplastic epidermis (1+) |
| | Dermal inflammation (1+) |
| Case 4991 B1: Control lesion | Surface exudation (2+) |
| | Hyperplastic epidermis (2+) |
| | Dermal inflammation (2+) |
| Case 4991 B2: Treated lesion | Surface exudation (−) |
| | Hyperplastic epidermis (2+) |
| | Dermal inflammation (2+) |
| Case 4991 C1: Control lesion | Surface exudative dermatitis (3+) |
| | Ulcerative boils (2+) |
| | Hyperplastic epidermis (2+) |
| | Dermal inflammation (3+) |
| Case 4991 C2: Treated lesion | Surface exudative dermatitis (−) |
| | Ulcerative boils (−) |
| | Hyperplastic epidermis (3+) |
| | Dermal inflammation (1+) |
| Case 4991 D1: Control lesion | Hyperplastic epidermis (3+) |
| | Dermal inflammation (3+) |
| Case 4991 D2: Treated lesion | Hyperplastic epidermis (3+) |
| | Dermal inflammation (1+) |

Key: − absent
1+ light
2+ medium
3+ severe

Conclusion

These results must be interpreted as being histopathological observations only. These results are presented in addition to the clinical observations of the lesions that were treated.

In general, and with due regard to the abovementioned limitations, it appears as if healing was promoted and inflammation reduced in the treated lesions.

The surface (shallow) exudative dermatitis (acute inflammation) did show accelerated healing in all cases. Hyperplastic epidermis (acantosis) is a chronic condition and thus showed little change upon treatment. The degree of dermal inflammation was also reduced in all except one of the treated lesions when compared to the original untreated lesions.

There were no controls or lesions that were left untreated for the same period of time as the treated lesions. Spontaneous healing can thus not be excluded as a contributing factor when interpreting these results.

Toxicity Studies in Experimental Animals

The applicant has undertaken acute and chronic toxicity studies which served to prove the safety and very low toxicity of oxifulvic acid.

Acute oral and dermal toxicity studies, acute dermal and eye irritation studies, skin sensitization studies as well as subchronic oral and dermal toxicity studies, in which the oxifulvic acid solution (25.4% concentrate) and the oxifulvic acid cream (formulated to contain 5.33% oxifulvic acid in this particular instance) were evaluated. The results of the investigations are summarized in Tables 5 and 6.

TABLE 5

25.4% Oxifulvic acid toxicity studies

| STUDY NUMBER | TYPE OF STUDY | RESULTS |
|---|---|---|
| 1388 | Acute oral toxicity in rats | $LD_{50}$ value >3380 mg/kg |
| 1389 | Acute dermal toxicity in rats | $LD_{50}$ value >5712 mg/kg |
| 1390 | Acute dermal irritation | Non-irritant |
| 1391 | Acute eye irritation | Non-irritant |
| 1392 | Skin sensitization | Weak skin sensitizer |
| 1520 | Subchronic oral toxicity in rats (90 day study) | Highest dose tested was 1000 mg/kg/day. No deaths or sick animals. Slight alterations in blood chemistry and slight decreases in body masses. |

TABLE 5-continued

25,4% Oxifulvic acid toxicity studies

| STUDY NUMBER | TYPE OF STUDY | RESULTS |
|---|---|---|
| 1530 | Subchronic dermal toxicity in rats (90 day study) | Highest dose tested was 1000 mg/kg/day (of the active substance) No deaths or sick animals. Slight alterations in blood chemistry and slight decreases in body masses. |

TABLE 6

5,33% Oxifulvic acid cream toxicity studies

| STUDY NUMBER | TYPE OF STUDY | RESULTS |
|---|---|---|
| 1393 | Acute oral toxicity in rats | $LD_{50}$ value >4147 mg/kg |
| 1394 | Acute dermal toxicity in rats | $LD_{50}$ value >8599 mg/kg |
| 1395 | Acute dermal irritation in rabbits | Slight irritant |
| 1396 | Acute eye irritation in rabbits | Non-irritant |
| 1397 | Skin sensitization in guinea pigs | Moderate skin sensitizer |
| 1512 | Subchronic dermal toxicity in rats (90 day study) | Highest dose tested was 1000 mg/kg/day. No deaths or sick animals. Slight alterations in blood chemistry and local irritation at site of application |

Discussion

The data shows that none of the products produced any measurable toxicity during the acute dermal or oral exposure tests.

During the sub-chronic oral and dermal toxicity studies with both substances very high doses were used. Animals were dosed with 1000 mg/kg/day of the active substance in the oxifulvic acid study. The 5.33% oxifulvic acid cream was applied to the skin of rats at a dose rate of 1000 mg/kg/day for a period of 90 days. No abnormal clinical signs were noticed and none of the animals died during the studies. The changes in the clinical pathology and body masses in the animals receiving the test item were relatively small.

The Antimicrobial Properties of Oxifulvic Acid

The antimicrobial properties of an oxifulvic acid solution (25.4 percent by mass of the fulvic acid) and a 4.5 percent by mass oxifulvic acid cream were evaluated in vitro on a number of well known pathogens. The results obtained are presented in Tables 7 and 8. The symbol + denotes growth, and the symbol − denotes no growth.

TABLE 7

Antimicrobial activity of 25.4% oxifulvic acid solution

| | Dilution | | | |
|---|---|---|---|---|
| Organism | 1:2 | 1:10 | 1:20 | 1:40 |
| β-Hemolytic streptococcus | − | − | − | + |
| Streptococcus faecalis | − | − | − | + |
| Klebsiella pneumoniae | − | − | − | + |
| Pseudomonas aeruginosa | − | − | − | − |
| Candida spp. | − | − | − | + |
| Escherichia coli | − | − | + | + |
| Proteus mirabilis | − | − | − | + |
| Staphylococcus aureus | − | − | + | + |

TABLE 8

Antimicrobial activity of 4,5% oxifulvic acid cream

| | Dilution | | |
|---|---|---|---|
| Organism | 1:2 | 1:10 | 1:20 |
| β-Hemolytic streptococcus | − | + | + |
| Streptococcus faecalis | − | + | + |
| Klebsiella pneumoniae | − | + | + |
| Pseudomonas aeruginosa | − | + | + |
| Candida spp. | − | + | + |
| Escherichia coli | − | + | + |
| Proteus mirabilis | − | + | + |
| Staphylococcus aureus | − | + | + |

Further, the efficacy of the 4.5 percent oxifulvic acid cream and a 25.4 percent by mass oxifulvic acid solution to inhibit the growth of bacteria and fungi was tested in accordance with the SABS method 730 (in vitro) on a few test organisms. The results obtained are set out in Table 9.

TABLE 9

Bacteriostatic and fungistatic efficacy of 4.5% oxifulvic acid cream and 25.4% oxifulvic acid solution

| | | Diameters (mm) of the zones of inhibition | | | | | |
|---|---|---|---|---|---|---|---|
| Samples | Dilution | Pseudomonas aeruginosa | Escherichia coli | Staphylococcus ureus | Aspergillus niger | Candida albicans | Streptococcus pyogenes |
| Solution | 25.4% | 29.4 | 29.36 | >29.0 | 18.83 | 118.36 | 22.71 |
| Solution | 5000 ppm | N/T | N/T | N/T | No zone | No zone | N/T |
| Solution | 1000 ppm | No zone | No zone | No zone | N/T | N/T | N/T |
| Solution | 1500 ppm | No zone | No zone | No zone | N/T | N/T | N/T |
| Cream | 4.5% | 15.6 | 14.74 | 28.8 | 9.66 | 9.58 | 13.39 |

N/T = not tested

From the aforegoing studies it can be seen that oxifulvic acid exhibits some measure of antimicrobial activity or bacteriostatic or fungistatic efficacy against some of the test organisms, even when formulated in a cream.

The 4.5 percent oxifulvic acid cream was subjected to a preservative efficacy test by the Microbiological Division of the SABS and it was found that the cream complied with the requirements of the USP 23 (1995).

Antiviral Activity of Oxifulvic Acid

Methods

The following viruses were tested:

Human herpes simplex virus type 1

Human adenovirus type 2

Simian rotavirus SA 11

Poliovirus type 1 Sabin vaccine strain

Coxsackie B virus type 1 laboratory strain

Coxsackie A virus type 9 laboratory isolate

Viruses were grown in either vervet monkey kidney cells or a primary liver cancer cell line (PLC/PRF/5). Stock virus suspensions were titrated to establish their titre and to prepare a viral suspension containing 100×50% tissue culture infectious dose (100 $TCID_{50}$)/200 µl.

Prevention of binding of viruses to the host cell: Monolayers of the appropriate cell cultures in 96-well microtitre trays were washed and starved for a minimum of 1 hr in serum-free MEM. After starvation, doubling dilutions of oxifulvic acid in serum-free MEM were added to each well together with 100 $TCID_{50}$ virus. The microtitre trays were incubated at 37° C. and examined daily, for 7 days, for CPE. Wells inoculated with 100 $TCID_{50}$ viruses and no oxifulvic acid acted as positive controls. The appearance of CPE indicated that no inhibition of binding had taken place.

Inhibition of viral replication in the host cell: Monolayers of the appropriate cell cultures in 96-well microtitre trays were washed and starved for a minimum of 1 hr in serum-free MEM. After starvation 100 $TCID_{50}$ virus was added to all wells and allowed to adsorb for 1–2 hrs. After adsorption, the unadsorbed viruses were washed from the wells using serum-free MEM. Thereafter doubling dilutions of oxifulvic acid, in serum-free MEM, were added to the appropriate wells. The microtitre trays were incubated at 37° C. and examined daily, for 7 days, for CPE. Wells inoculated with 100 $TCID_{50}$ viruses and no oxifulvic acid acted as positive controls. The appearance of CPE indicated that no inhibition of viral replication had taken place.

Results

The effects of oxifulvic acid on the binding of viruses to the host cells as well as on the replication of viruses can be seen in Tables 10A and 10B.

TABLE 10A

Effects of oxifulvic acid on the binding of viruses to the host cells

| Virus | Lowest concentration at which 100% viral inhibition was noted at day 6 or 7 post infection (mg/ml) | Lowest concentration at which limited viral inhibition was notices (mg/ml) |
| --- | --- | --- |
| Herpes simplex virus type 1 | 1.875 | 0.234 |
| Human adenovirus type 2 | 3.75 | 0.937 |
| Simian rotavirus SA 11 | 1.875 | 0.058 |
| Polio virus type 1 | 1.875 | 0.468 |
| Coxsackie B virus type 1 | 1.875 | 0.937 |
| Coxsackie A virus type 9 | 1.875 | 1.875 |

TABLE 10B

Effects of oxifulvic acid on the replication of viruses

| Virus | Lowest concentration at which 100% viral inhibition was noted at day 6 or 7 post infection | Lowest concentration at which limited viral inhibition was noticed |
| --- | --- | --- |
| Herpes simplex virus type 1 | 1.875 | 0.937 |
| Human adenovirus type 2 | 3.75 | 1.875 |
| Simian rotavirus SA 11 | 3.75 | 0.234 |
| Polio virus type 1 | 0.468 | 0.234 |
| Coxsackie B virus type 1 | 1.875 | 0.937 |
| Coxsackie A virus type 9 | 1.875 | 0.468 |

Discussion

Oxifulvic acid prevented the binding of the six experimental virus cultures between 1.87 mg/ml and 3.75 mg/ml whereas inhibition of viral replication was inhibited at concentrations between 0.469 mg/ml and 3.75 mg/ml. Limited inhibition of viral replication was noted at a concentration as low as 0.103 mg/ml in the case of simian rotavirus SA 11.

Oxifulvic acid is therefore a compound that
 i) scavenges the neutrophil-derived pro-inflammatory reactive oxidant superoxide;
 ii) decreases production of the lymphocyte-derived pro-inflammatory cytokine IL-2;
 iii) inhibits a mixed lymphocyte reaction typical of a transplanted organ rejection reaction;
 iv) has in vitro activity against Gram positive, Gram negative, as well as fungal and viral human pathogens;
 v) inhibits a contact hypersensitivity reaction induced in dinitrofluorobenzene sensitized mice as effectively as generally used anti-inflammatory agents such as dichlophenac sodium and betamethasone (these two agents are however associated with serious adverse side effects);
 vi) has in vivo anti-inflammatory activity against pyotraumatic dermatitis in cats and dogs; and
 vii) has very low toxicity in experimental animals.

REFERENCES

1. Bergh J J, Cronjé I J, Dekker J, Dekker T G, Gerritsma M L and Mienie L. 1997. Non catalytic oxidation of water-slurried coal with oxygen: identification of fulvic acids and acute toxicity. *Fuel*, 76 (2):149–154.
2. Clark N N, Chipman J K. 1995. Absorption of 3-chloro-4-(dichloromethyl)-5-hydroxy-2[5H]furanone (MX) through rat small intestine in vitro. *Toxicol Lett*, 81(1):33–38.
3. Gramsch H. 1961. Ein Beitrag zur Behandelung der Gastropatien. *Med Monatsschr*, 15:658–687
4. Lopez-Fernandez M F, Blanco-Lopez M J, Castineira M P, Batlle J. 1992. Further evidence for recessive inheritance of von Willebrand disease with abnormal binding of von Willebrand factor to factor VIII. *Am J Hematol*, 40:20–27.
5. MacCarthe P, Clapp C E, Malcolm R L, Bloom P R. 1990. Humic substances in soil and crop sciences: selected readings. Proceedings of a symposium by International Humic substances Society, Soil Science Society of America, Americal society of Agronomy and Crop Science Society of America, Chicago, Ill., Dec. 2, 1985.
6. Malcolm R L. 1985. The geochemistry of stream fulvic and humic substances p. 181–209. In Aiken G R et al (ed.) Humic substances in soil, sediment and water: Geochemistry isolation and characterization. Wiley-Intersciene, New York.
7. Motohisa S, Yoshinori H, Shuzo K. 1974. Humic acids for treatment of skin disorders, In:C A 80, p.283 100222u, Patent Japan. Kokai 7392, 524.
8. Peng A, Xu L Q. 1987. The effects of humic acid on the chemical and biological properties of selenium in the environment. *Sci Total Enviro,* 64(1–2):89–98.
9. Reichert B. 1966. Huminsäuren und inhre Derivate in der modernen Therapie. *Dtsh Apoth,* 18:204–206.
10. Rheins L A, Barnes B, Amornsiripanitch S, Collins C E, Nordlund J J. 1987. Suppression of the cutaneous immune response following topical application of prostaglandin $PGE_2$.
11. Salz H. 1974. Salhumin-Gel, ein Lokaltherapeutikum mit hyperämisierender, entzündungshemmender und analgetischer Wirkung. *Med Monatsschr,* 28:548–530.
12. Solovyeva V P, Lotosh T D. 1984. Biologically active peat substances body resistance stimulators. Dublin: Ireland. Proceedings of the $7^{th}$ International Peat congress, 4, 428–434.
13. Stevenson F J. 1982. Humus chemistry: Genesis, composition, reactions. Chapter 9. Reactive functional groups of humic substances. Wiley-Interscience, New York.
14. Wang C, Wang Z, Peng A, Hou J, Xin W. 1996. Interaction between fulvic acids of different origins and active oxygen radicals. *Sci China C Life Sci,* 39(3) :267–275.

What is claimed is:

1. A method of treating a subject presenting inflammation, acne, eczema, a bacterial infection, a viral infection, or any combination thereof, comprising administering to said subject a composition comprising fulvic acid, or a salt, ester or derivative thereof.

2. The method of claim 1 in which the composition is administered orally or topically.

3. The method of claim 1 in which the fulvic acid, or salt, ester or derivative thereof is oxifulvic acid or a salt, ester or derivative thereof.

4. The method of claim 2 in which the fulvic acid, or salt, ester or derivative thereof is oxifulvic acid or a salt, ester or derivative thereof.

5. The method of claim 3 in which the oxifulvic acid, or salt, ester or derivative thereof comprises 11.5 to 15.5 milliequivalents/g of total acid groups, 8.5 to 12.5 milliequivalents/g of carboxylic acid groups and 2.3 to 3.7 milliequivalents/g of phenolic groups.

6. The method of claim 4 in which the oxifulvic acid, or salt, ester or derivative thereof comprises 11.5 to 15.5 milliequivalents/g of total acid groups, 8.5 to 12.5 milliequivalents/g of carboxylic acid groups and 2.3 to 3.7 milliequivalents/g of phenolic groups.

7. The method of any one of claims 1–6 in which the subject is a human.

8. The method of any one of claims 1–6 in which the subject is a non-human animal.

* * * * *